US008153015B2

(12) United States Patent
Salvati et al.

(10) Patent No.: US 8,153,015 B2
(45) Date of Patent: *Apr. 10, 2012

(54) ULTRA-PASSIVATION OF CHROMIUM-CONTAINING ALLOY AND METHODS OF PRODUCING SAME

(75) Inventors: Lawrence Salvati, Goshen, IN (US); Sophie Xiaofan Yang, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 340 days.

This patent is subject to a terminal disclaimer.

(21) Appl. No.: 12/193,092

(22) Filed: Aug. 18, 2008

(65) Prior Publication Data
US 2009/0175918 A1 Jul. 9, 2009

Related U.S. Application Data

(60) Provisional application No. 60/956,778, filed on Aug. 20, 2007.

(51) Int. Cl.
*C25F 3/02* (2006.01)
(52) U.S. Cl. ............ 216/28; 216/32; 216/57; 216/67; 216/75; 216/76; 216/83; 216/100; 216/101; 216/108; 427/2.24
(58) Field of Classification Search .......... None
See application file for complete search history.

(56) References Cited

U.S. PATENT DOCUMENTS

| 4,421,593 | A | * | 12/1983 | Curtis et al. ............ 216/48 |
| 2003/0125808 | A1 | * | 7/2003 | Hunter et al. ............ 623/18.11 |
| 2006/0157159 | A1 | * | 7/2006 | Yeung et al. ............ 148/239 |
| 2007/0083269 | A1 | * | 4/2007 | Onate Dela Presa et al. ............ 623/23.5 |
| 2008/0071382 | A1 | * | 3/2008 | Kumar et al. ............ 623/23.57 |
| 2009/0204213 | A1 | * | 8/2009 | Liao et al. ............ 623/11.11 |

FOREIGN PATENT DOCUMENTS

| EP | 0520721 | | 12/1992 |
| EP | 2002854 | | 12/2008 |
| JP | 2007260247 | A * | 10/2007 |
| WO | WO 2008/018820 | | 2/2008 |

OTHER PUBLICATIONS

European Patent Application No. EP-08162563: European Search Report dated Apr. 30, 2009, 2 pages.

* cited by examiner

*Primary Examiner* — Anito Alanko

(57) ABSTRACT

The invention concerns article having a surface oxide layer up to 20 nm thick, the surface oxide layer comprising chromium and cobalt oxides where the atomic ratio of Cr/Co is more than 3. The invention also concerns methods for treating a chromium containing material, said method comprising contacting said material with a gas plasma under conditions effective to oxidize at least a portion of the material; and contacting said material with an acid. The treated surface is corrosion resistant and can be used in orthopedic implants, especially the wear surface of the orthopedic implant to reduce wear, and other corrosive environment.

23 Claims, 6 Drawing Sheets

Metal on Metal (MoM) Wear Simulator Testing

ULTRA-PASSIVATION OF CHROMIUM-CONTAINING ALLOY AND METHODS OF PRODUCING SAME

RELATED APPLICATION

This application claims benefit of U.S. Provisional Application No. 60/956,778, filed Aug. 20, 2007, which is incorporated herein in its entirety.

BACKGROUND OF THE INVENTION

Metal-on-metal (MOM) prosthesis implants have been around since the 1960s. Presently, the use of metal-on-metal implants has been increasing due to the fact that historically MOM systems have shown better than two orders of magnitude less wear than metal-on-polyethylene (MOP) systems. However, in the case of MOM devices, there is still concern regarding the long term effects of in vivo metal ion release due to corrosion and/or wear of the metal components.

The corrosion resistance of CoCrMo alloys is thought to be due to the existence of a natural metal oxide layer on the alloy surface. The major components of this oxide layer are cobalt oxide and chromium oxide. Because chromium oxide is much more resistant to leaching by body fluids than cobalt oxide, the corrosion resistance of the alloy depends on the continuity, thickness and chromium oxide content of the layer.

In the orthopedic industry, CoCr implants are routinely treated by immersion in 30% nitric acid solution at an elevated temperature (54° C.). It is believed by many in the industry that passivating CoCr materials with nitric or citric acid leads to the production of a corrosion resistant surface by forming a thin transparent Cr-oxide film. It is this layer that they believe imparts the corrosion resistance to CoCr implant materials. These beliefs are based on work published for Stainless Steel passivation. In reality, the surface of a nitric (citric) acid passivated surface has a surface composition of approximately 50:50 Co and Cr.

MOM implants are also subject to weight loss caused by the continuous friction of two contacted surfaces moving in body fluid. As these surfaces contact each other, the interaction of asperities or surface roughness causes wear.

To date, most efforts to reduce wear in MOM systems have focused primarily on reducing surface roughness and/or surface asperities. In particular, many investigators believe that removing surface "carbide asperities" will dramatically reduce break-in wear and yield a lower wear system. Many attempts have been made to remove surface carbides via enhanced polishing methods and heat treatment processes designed to "dissolve" the carbides into the alloy. These efforts, however, have produced little impact in terms of a significant reduction in break-in wear. Thus, there remains a need in the art to reduce break-in wear in prosthesis devices.

SUMMARY OF THE INVENTION

One aspect of the present invention concerns chromium containing, such as CoCrMo, articles having a surface oxide layer up to 20 nm thick, said surface oxide layer comprising chromium and cobalt oxides where the atomic ratio of Cr/Co is >3. In some aspects, the invention concerns a method comprising: contacting the chromium containing material with a gas plasma under conditions effective to oxidize at least a portion of the material; and contacting the material with an acid under conditions effective to form a robust Cr-oxide surface layer substantially thicker than that produced using the conventional process described above.

The material can be contacted with the gas plasma before it is contacted with the acid or the material can be contacted with the acid before and after it is contacted with the gas plasma.

In some embodiments, the acid includes nitric acid or hydrochloric acid. In one embodiment, the acid includes hydrochloric acid and the first acid passivation treatment is followed by a second acid passivation treatment using an acid comprising nitric acid.

The gas plasma used in the methods of the invention can be derived from an oxidative gas or from a mixture of gases comprising oxidative gas and optionally one or more inert gases. One preferred oxidative gas is oxygen. Inert gases include nitrogen, argon and helium. In certain embodiments, the material is contacted with the gas plasma for about 5 to about 120 minutes. In some embodiments, the contacting of the material with the gas plasma is performed at a power of about 100 to about 1000 watts. In some embodiments, the mixture of gasses comprises at least 3% (v/v) percent oxidative gas. Other embodiments contain 100% (v/v) percent oxidative gas.

The invention also concerns articles made by the methods described herein. In some embodiments, the invention concerns articles comprising cobalt and chromium, the article having a surface comprising oxides where the oxides are characterized with a Cr/Co>3 (as measured by XPS). In certain embodiments, the oxides are characterized by a Cr/Co~7. In some articles, the surface oxide is 3-8 nm thick. This highly enriched chromium oxide layer impart a significantly higher corrosion resistance versus the relatively thin (~1-2 μm) passive film formed via the conventional passivation process.

Some articles are designed to be implantable into a mammal. Certain of these articles are joint replacement prosthesis or component thereof. Such prosthesis include hip or knee replacement prosthesis.

In some embodiments, the treated material is used on a wear surface, especially an orthopedic implant wear surface to reduce wear.

Some articles are very corrosion resistant and they can be used in corrosive environment, including acid or alkaline environments. The inventive passivation film can reduce the ion release in simulated body fluid.

The invention also concerns methods comprising implanting a prosthesis comprising chromium and cobalt in a human or animal body in contact with bone, wherein at least a portion of the prosthesis in contact with said bone comprising a surface having an exterior oxide layer of up to 20 nm in thickness that is highly enriched in chromium oxide.

a) polished, b) after 30% $HNO_3$ treatment at 54° C. for 0.5 hr (representative of the conventional passive method) and c) after $O_2$ plasma treatment with 1000 w, 300 mTorr, 250 sccm for 1 hr+30% $HNO_3$ at 54° C. for 0.5 hr (an inventive process). The inventive treatment results in a substantially thicker surface oxide than the conventionally passivated surface (about 5 nm vs 2 nm). In addition, the Cr/Co ratio measured for the surface treated using the inventive process (Cr is dominant and Co is near 0) is also enhanced relative to the conventionally passivated surface (Cr/Co=0.2).

Figure 1:
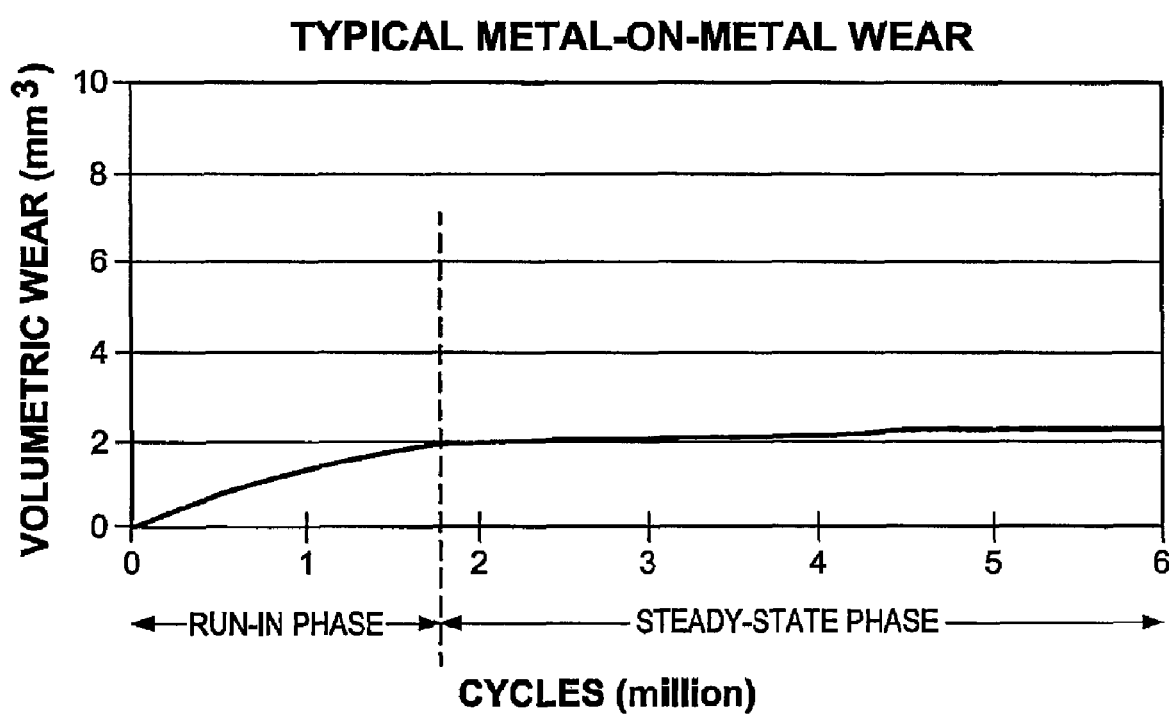
FIG. 1 shows a typical wear graph for MOM prosthesis devices. The graph is divided into two phased: the initial run-in phase and the second steady state phase. The X-axis is the cycle number and the Y-axis is the accumulative volume loss of the prosthesis. The slope of the graph is the volume loss rate. The graph shows that a majority of the volume loss happens in the initial stage—run-in phase.
Figure 2:
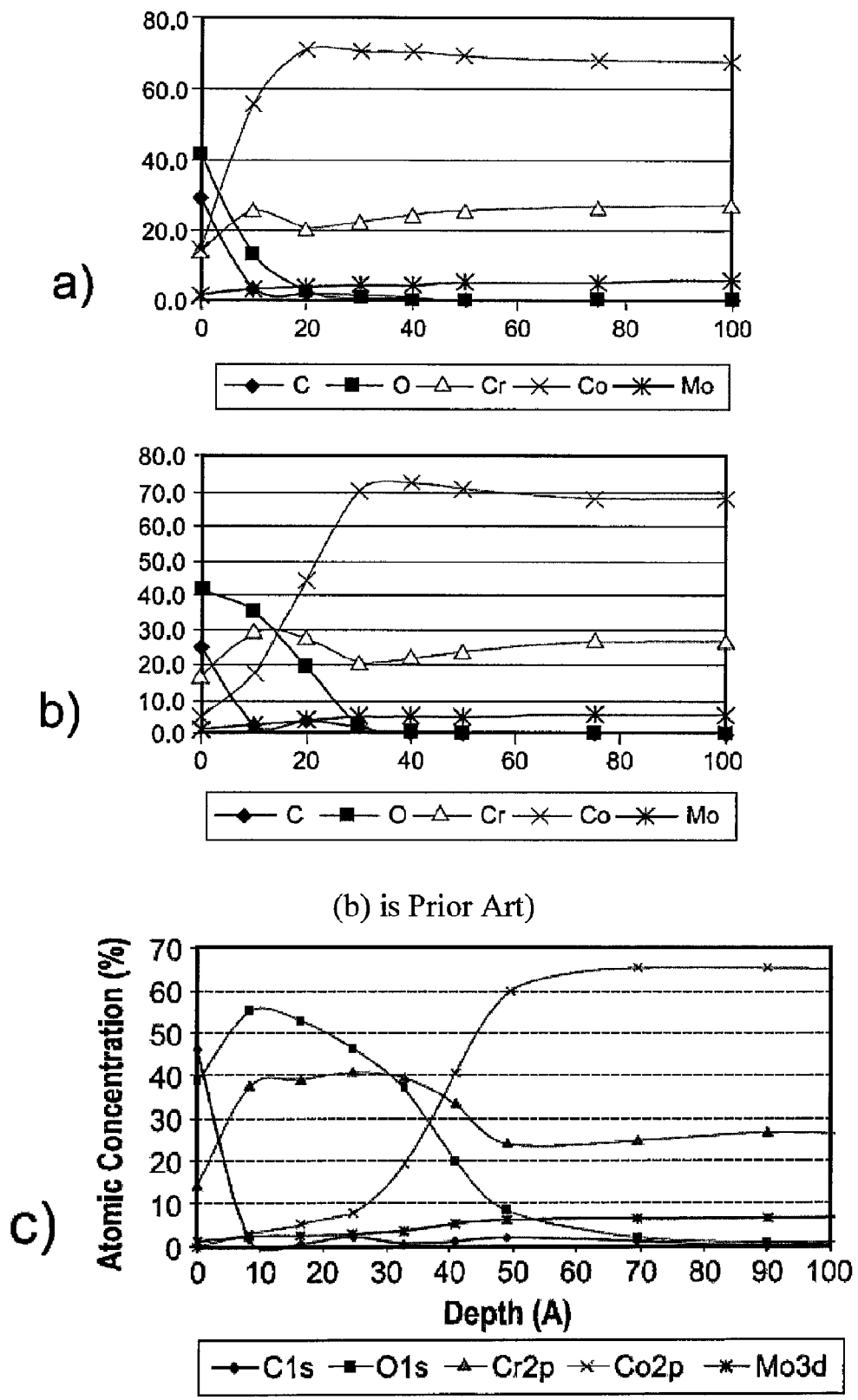
FIG. 2 shows XPS sputter depth profile data obtained on CoCrMo test disks.
Figure 3:
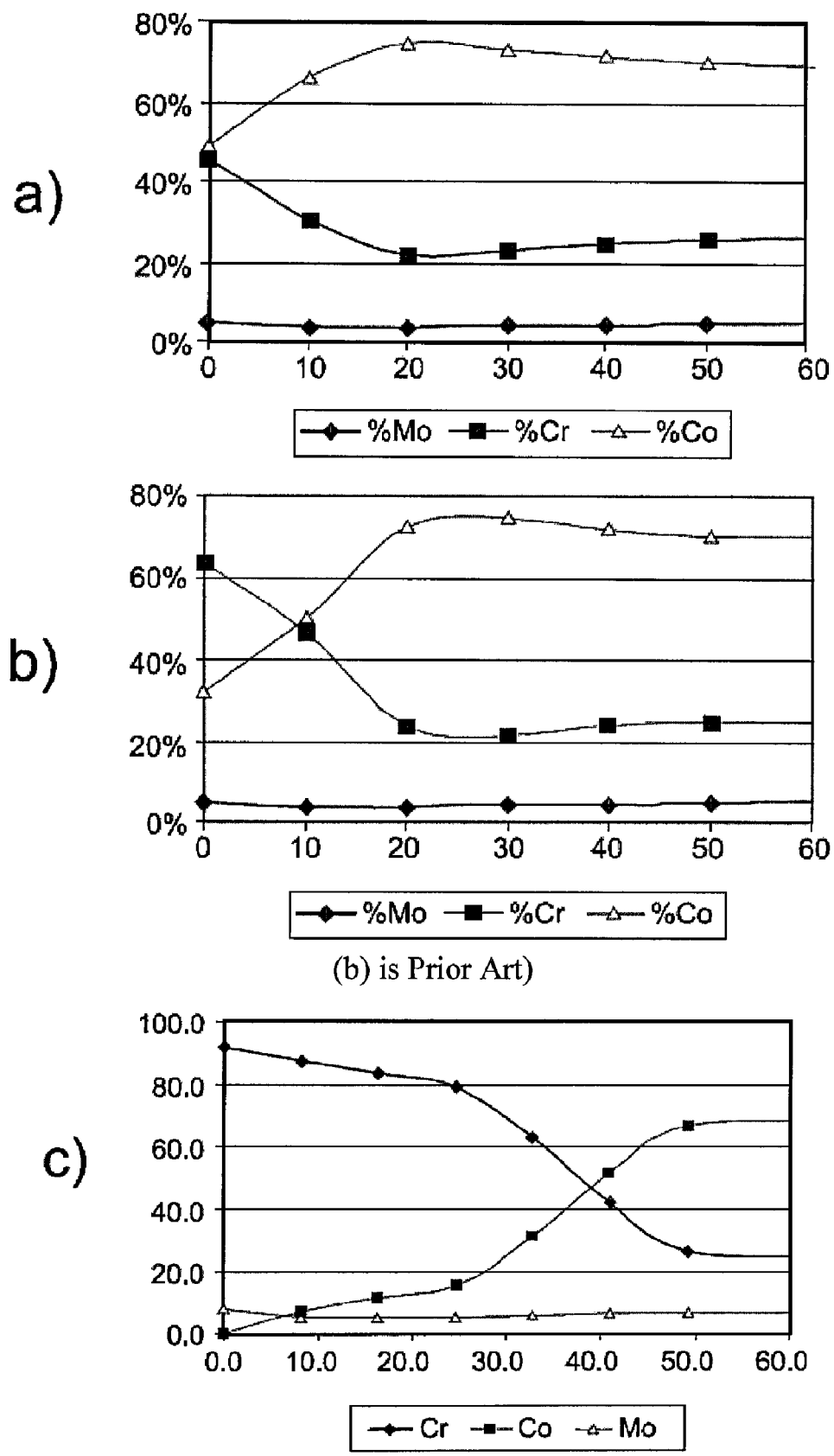

FIG. 3 shows the same XPS sputter depth profile data as shown in FIG. 2, but the O and C profile data has been removed and the atomic concentration for the metal atoms has been renormalized. a) polished, b) after 30% $HNO_3$ at 54° C. for 0.5 hr, (the conventional passive method) and c) after $O_2$ plasma treatment with 1000 w, 300 mTorr, 250 sccm for 1 hr+30% $HNO_3$ at 54° C. for 0.5 hr (an inventive treatment). The O and C profile data was removed and the atomic concentration was renormalized. The profile shows that Cr/Co ratio in the inventive treatment surface oxide film (c) is the highest.

Figure 4:
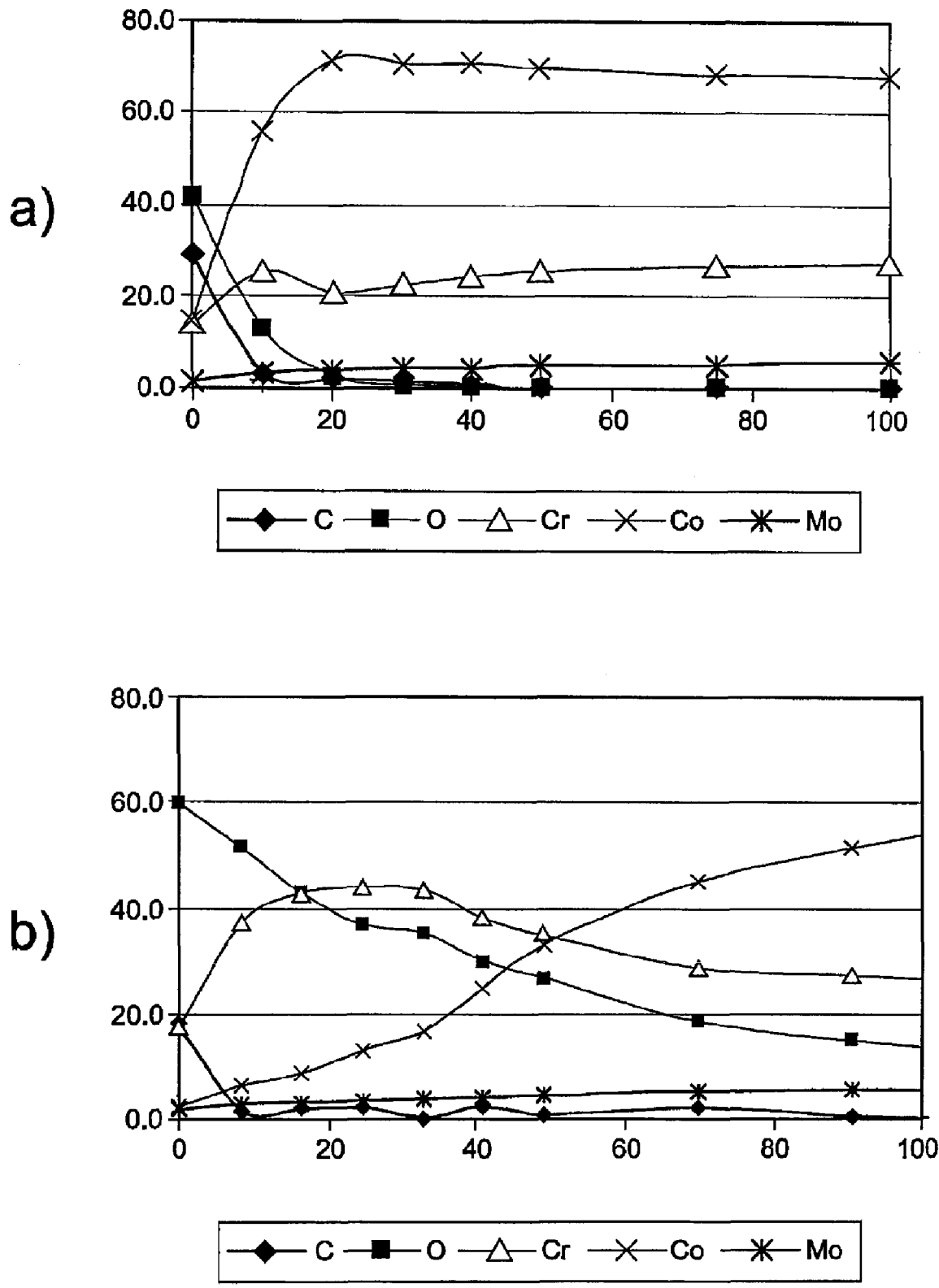

FIG. 4 shows XPS sputter depth profile data obtained on CoCrMo test disks: a) polished and b) after inventive treatment: $O_2$ plasma treatment with 1000 w, 300 mTorr and 250 sccm for 1 hr+6N HCl treatment for 1 hr.

Figure 5:
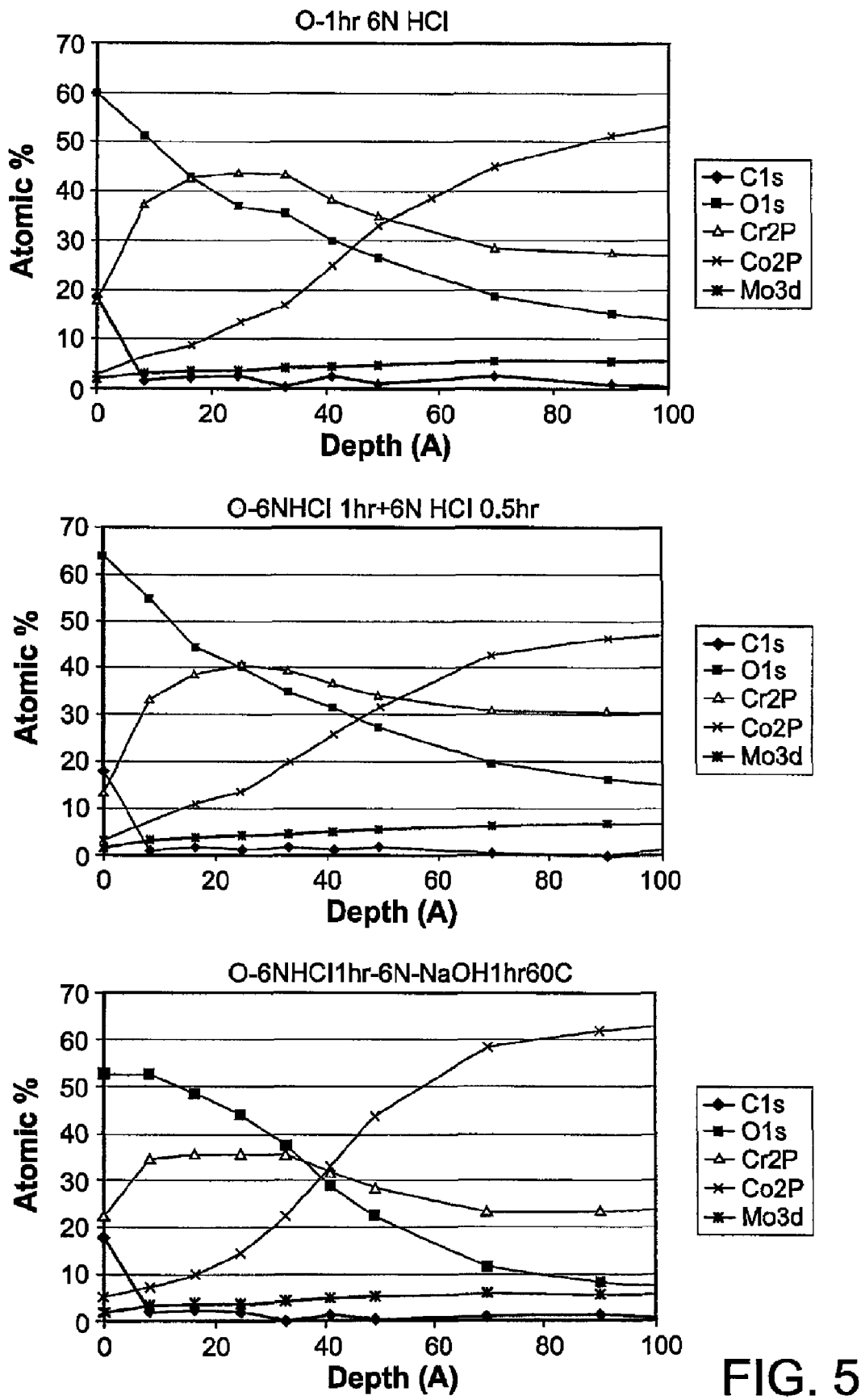

FIG. 5 shows the XPS sputter depth profile data on the test disks: a) after 1 hr $O_2$ plasma treatment with 1000 w, 300 mTorr and 250 seem+1 hr 6N HCl treatment at room temperature, b) after treated with above method, the surface was put into 6N HCl at 60° C. for 0.5 hrs, and c) after treated with above method, the treated surface was put into 6N NaOH at 60° C. for 1 hr. The inventive passive film is corrosion resistant in both acid and alkaline solutions.

Figure 6:
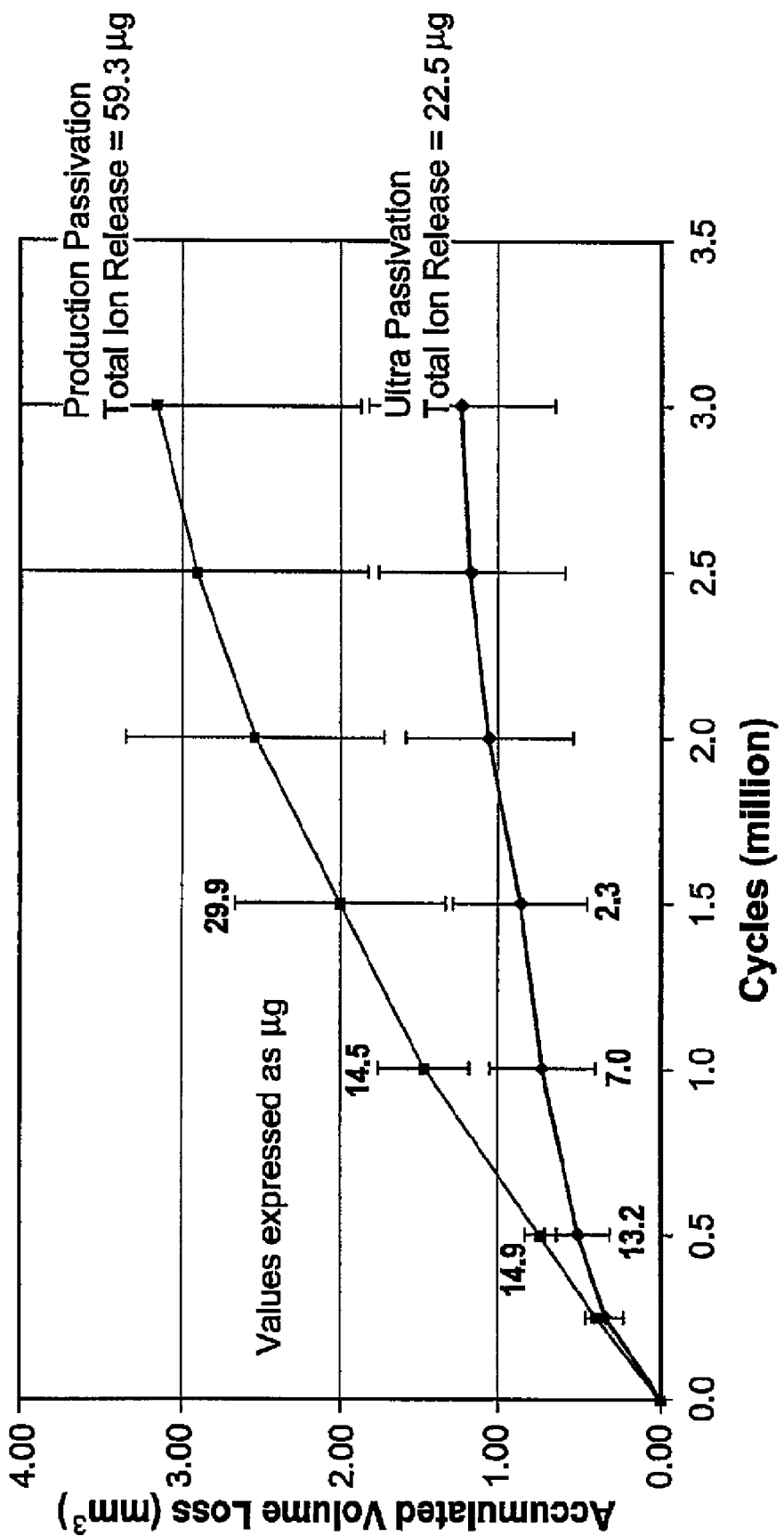

FIG. 6 shows Hip simulator wear graph comparing the parts after 3 million cycle wear tests. The one after inventive treatment (30% $HNO_3$, at 54° C. for 0.5 hrs+$O_2$ plasma treatment, 1000 w, 300 m Torr, 250 sccm for 1 hr+30% $HNO_3$, at 54° C. for 0.5 hrs) is about 3-fold reduction in the break-in wear than the one after the conventional passivation treatment (30% $HNO_3$, at 54° C. for 0.5 hrs). The data shows that the ion release on the passivated surface of the invention is significantly reduced.

DETAILED DESCRIPTION OF ILLUSTRATIVE EMBODIMENTS

The present invention relates, in part, to chromium containing articles and devices having thick and Cr highly enriched surface oxide layers. The invention also relates to processes to make improved wear surfaces on chromium containing materials. This surface preferably has a strengthened passive film, which can reduce ion release rates by decreasing the corrosion rate. Wear is believed to be reduced by protecting the wear surface from selective corrosion in surrounding carbide areas. One type of process described herein includes plasma oxidation and acid treatment. The acid treatment can be conducted after plasma oxidation or both before and after plasma oxidation.

Certain processes involve the steps of subjecting a cobalt- and chromium-containing implant material to an energetic, oxidative gas plasma and treating the implant material with acid. This acid treatment can be achieved after plasma oxidation or before and after plasma oxidation. The plasma treatment process can be achieved using an oxidative gas such as oxygen or a mixture of oxidative gases and inert gases at a power of between 100 and 1000 watts for a time of between 5 minutes to 120 minutes. Compared with the oxide layer obtained from the conventional $HNO_3$ passivation process, the one obtained from the inventive process preferably is thicker and the Cr/Co ratio is higher. The enhancement of the oxide is believed to reduce the amount of metal ion release due to corrosion and/or wear.

In certain methods of the invention, surfaces are treated with a gas plasma under conditions effective to oxidize at least a portion of the surface. The oxidative component of the gas can comprise oxygen, water, hydrogen peroxide, or mixtures thereof. In some embodiments, the oxidative gas plasma can be formed, for example, from oxygen, a mixture of oxygen with air, or with one of the foregoing along with one or more non-reducible gases. Non-reducible gases include argon, nitrogen, neon, helium, xenon, and krypton. In some embodiments, argon is preferred. In some preferred embodiments, the amount of oxygen in the gas is greater than 3%. In some preferred embodiments, the amount of oxygen in the gas is 3%-100%

Typically, a plasma is generated by creating an electrical discharge in a gaseous atmosphere under suitable pressure conditions. A typical plasma treatment system has a chamber capable of being maintained at a desired pressure (typically atmospheric or below). The surface to be treated is placed with the chamber with the selected gas and an appropriate electrical discharge is applied to the chamber. A number of gas plasma treatment systems suitable for use in the practice of the present invention are commercially available and such systems are generally known.

The energy source used in the gas plasma oxidation is one capable of supplying a sufficient amount of energy to ionize at least a portion of oxidative gas to form a gas plasma. At least three power sources have been widely used in practice to supply the energy. These include DC electrical energy, radio frequency (RF) energy, and microwave energy. In methods of the present invention, any suitable energy source, including the three mentioned herein can be utilized. It is generally recognized, however, that RF energy sources typically have the greatest sensitivity and are the freest from interference. Thus, in some embodiments, a RF energy source is preferred.

The amount of energy utilized to form the plasma is typically from about 100 to about 1000 watts. In some preferred embodiments, the amount of energy is from about 800 to about 1000 watts.

The gas plasma treatment of the surface is typically performed for about 5 to about 120 minutes. In some embodiments, the time is from about 30 to about 90 minutes. In other embodiments, however, the time is at least 60 minutes.

The pressure at which the gas plasma oxidation is performed is typically from atmospheric pressure to sub-atmospheric pressure. In some embodiments, the pressure is from about 200 mTorr to about 400 mTorr. In certain embodiments, the pressure is about 300 mTorr.

During the gas plasma oxidation, the flow rate of the gases through the oxidizing chamber is generally from about 100 standard cubic centimeters per minute (seem) to abut 500 sccm. In one preferred embodiment, the flow rate is about 150-350 sccm (250 preferred in some embodiments).

In some embodiments, the acid includes nitric acid ($HNO_3$), hydrochloric acid (HCl), sulfuric acid ($H_2SO_4$) or citric acid. In some embodiments, the preferred acid includes nitric acid and HCl. The surface is preferably contacted with a liquid acid at a concentration that suitably passivates the surface. One preferred concentration range of the acid is about 2M-8M In certain embodiments, the acid concentration is about 3M-6M. The surface can be treated for a time sufficient to develop a thick robust Cr rich surface layer. In some embodiments, the surface is contacted with the acid for about 20 to about 120 minutes (30-90 min in some embodiments, or about 60 min in other embodiments). The treatment can occur at a temperature of 10° C. to 90° C. In certain embodiments, the preferred temperature is about 20° C. to about 60° C.

In some embodiments, more than one acid passivation step can be utilized. The acid passivation step can be conducted after plasma oxidation or conducted before and after plasma oxidation. As used herein, the term "before" includes intervening events that may occur (for example, "before" need not be "immediately before"). Certain embodiments have more than one acid treatment step after the plasma oxidation. For example, an acid treatment step using an acid comprising hydrochloric acid followed by another acid treatment step using nitric acid can be utilized.

"Passivation", according to ASTM A380, is "the removal of exogenous iron or iron compounds from the surface of stainless steel by means of a chemical dissolution, most typically by a treatment with an acid solution that will remove the surface contamination, but will not significantly affect the stainless steel itself." In addition, it also describes passivation as "the chemical treatment of stainless steel with a mild oxidant, such as a nitric acid solution, for the purpose of enhancing the spontaneous formation of the protective passive film.

In the context of corrosion passivation is the spontaneous formation of a non-reactive surface film that inhibits further corrosion. This layer is usually an oxide or nitride that is a few atoms thick.

In the context of CoCrMo implant materials the XPS sputter depth profile presented in FIG. 2b illustrates the typical surface and near surface composition of a conventionally passivated material, i.e treated in 30% nitric acid solution.

"Ultra passivation" is the inventive process described here in whereby the surface, CoCrMo for example, is first treated in an oxygen plasma followed by an acid treatment. The surface (near surface) chemistry typical for materials treated using this process is shown in FIG. 2c. The inventive passivation process produces a significantly thicker protective surface oxide layer relative to the conventional process (FIG. 2b).

By "surface," in reference to a device or other article, it is intended to mean the outermost region of the device or article. In some cases, the surface of a device or article can have a metal oxide layer up to 20 nm thick. Some devices or articles can have a plurality of surfaces having different composition.

Surfaces suitable for treatment with the methods of the instant invention include those that are found on implantable devices (such as knee and hip replacement prostheses) and/or otherwise contain cobalt and chromium. Some metal implants are fabricated from surgical grade cobalt-chromium-molybdenum (CoCrMo) alloys because these alloys show good corrosion and wear resistance.

At various points in the processes of the instant invention, the substrate surface can optionally be cleaned using typical usual cleaning procedures, such as degreasing with detergent or an alkaline solution. Ultrasonic cleaning in detergent, followed by ultrasonic cleaning in water and drying, may degrease the substrate surface. In some embodiments, the entire implant is cleaned. In other embodiments, only a portion of the implant will be cleaned. One skilled in the art will readily appreciate that there may be a desire to perform an initial cleaning step before treating the surface with the processes disclosed herein. It may be desired to clean the surface between steps of the processes and/or at the end of the processes disclosed herein. Some cleaning steps might involve rinsing with soaking in water and followed by drying the surface.

The primary action of this treatment process is to impart a higher/improved corrosion resistance to the CoCr materials. The improved corrosion resistance results from the formation of a strengthened oxide layer with a high Cr/Co ratio on the device surface. While not wanting to be bound by theory, we believe that the enhanced corrosion resistance also leads to lower wear and/or metal ion release. We further feel that this treatment process should also improve the overall corrosion resistance of CoCr materials used in other applications. This benefit would include non-articulating surfaces as well as metal on poly or metal on ceramic applications.

The invention is illustrated by the following examples which are intended to illustrative and not limiting.

EXAMPLES

Except where noted, all tests were conducted on the ASTM F-1537 CoCrMo polished disks. The finished disks were 2 mm thick and 25 mm in diameter. The surface of the disks was polished to a mirror finish (0.1 μm) then rigorously cleaned in an Alconox solution in an ultrasonic bath. This step was followed with two (2) successive 3 minute RO (reverse osmosis) water rinse treatments.

Plasma treatments were performed in a PVA TePla Model 7200 Plasma Processing System by placing the sample CoCr disks in an aluminum tray located in the center of the chamber. Power settings for the plasma treatments were variable between 100 to 1000 watts. The examples presented here were conducted at 1000 watts (w), but 500 w and 800 w were also found to yield similar results. After placing sample disks into the plasma system, the chamber was evacuated to approximately 30 mTorr. After the chamber was evacuated, oxygen ($O_2$) was introduced into the chamber to 300 mTorr with a flow rate of 250 sccm. The treatment time used in the examples was 1 hour. The operation of the plasma treatment process was conducted under computer control, which included establishing and maintaining the process gas treatment "recipe".

X-ray photoelectron spectroscopy (XPS) data was acquired using a Physical Electronics (PHI) Quantara SXM instrument. The system uses a monochromatic AlKα x-ray source that emits photons at 1486.6 eV. The anode was run at a power of 45 watts (15 KeV). The typical base vacuum inside the spectrometer was $5 \times 10^{-9}$ torr. The analysis area for the XPS depth profile acquisitions was set at 200 μm. Sputtering for the XPS depth profiling was accomplished using energetic (2.0 keV) Ar ions rastered over a 2×2 mm area. The XPS depth profile data presented here is shown relative to depth quoted in Angstroms (Å). The sputter rate was determined using a 1000 Å $SiO_2$/Si calibration standard. The depth profile is displayed as atomic concentration (A.C.) versus sputter depth in Angstroms (Å). The sputter depth values in the graphs are calculated by multiplying the calibrated sputter rate (discussed above) and the sputter time. The A.C. values represent a normalized elemental atomic composition for each of the species listed. The numbers are calculated based on the XPS peak area and corrected with standard calibration factors resident in the data analysis software provided by the vendor.

Example 1

Clean and polished 25 mm diameter CoCrMo (F 1537) disks were placed on the center rack of the plasma chamber. The plasma chamber was evacuated to a base pressure of 30 mTorr then backfilled to 300 mTorr with $O_2$ (flow rate=250 sccm). The CoCr test disks were treated at an RF power setting of 1000 watts for 1 hour. After allowing the samples in the chamber to cool to room temperature, the chamber was backfilled with dry-$N_2$ and the test disks were removed. The plasma modified CoCrMo disks were then submitted for passivation using 30% $HNO_3$ for 30 minutes at a temperature of 54° C. At this stage the surface chemistry of the modified test disks was evaluated using X-ray Photoelectron Spectroscopy (XPS). More specifically, the XPS analyses were conducted as sputter depth profiles, which entail interleaving argon (Ar) ion sputtering with XPS analyses. The Ar ion sputtering interacts with the topmost surface atoms causing them to be removed at controllable rate. In the present analysis the sputter removal rate was calculated to be approximately 80 Å/min relative to the $SiO_2$ standard. The resulting depth profile data obtained for the modified test disks is shown in FIG. 2. This figure contains XPS sputter depth profiles obtained for CoCrMo test disks of polished (2a), treated with the conventional passivation method (30% $HNO_3$ at 54° C. for 0.5 hr) (2b) and treated with an inventive passivation method ($O_2$ plasma treatment at 1000 w, 300 mTorr, 250 sccm for 1 hr followed by 30% $HNO_3$ at 54° C. for 0.5 hr) (2c). The profile data is displayed with depth (plotted as Å removed) in the X-direction and atomic concentration (A.C.) in the y-direction. The data provides a 3-dimensional picture that shows the elemental composition of the uppermost atomic layers (approximately 10-40 nm) of the sample material. The top plot FIG. 2a shows the XPS sputter depth profile representative of a polished CoCrMo test disk surface. The data shows that the topmost surface of this sample contains equal concentrations of Co (x) and Cr (▲), or the Cr/Co ratio on the surface is about 1. The data further shows the presence of a very thin (approximately 1 nm) surface oxide layer, which is evident from the rapid decline in the oxygen (■) signal. At a depth of about 2 nm, the A.C. composition measured by XPS reflects the bulk stochiometry of the alloy. The XPS depth profile data in FIG. 2b shows the surface after conventional treatment. The thickness of the oxide layer is about 2 nm and Cr/Co ratio is about 2. The XPS profile collected for the inventive process treated an "ultra-passivated" sample (FIG. 2c) indicates that the passivation process used for this sample produced a much thicker oxide layer. In this instance the relative depth of the oxide layer is approximately 5 nm. More importantly, the data further shows that the composition of the surface oxide layer is predominantly a Cr-oxide, and while not wanting to be bound by theory, is most likely $Cr_2O_3$. Again, this interpretation is based on the elevated concentrations of Cr (▲) and O (■) within the topmost 4-5 nm coupled with the fact that the cobalt signal (x) was well below 10% (atomic) over this same depth range.

The same three XPS sputter depth profiles previously shown in FIG. 2 are reproduced in FIG. 3, but in this case the O and C traces have been removed and the metal A.C. values renormalized. This figure is included to more accurately illustrate how the inventive "ultra-passivation" process alters the metal atom composition of the near surface region. This figure clearly illustrates the fact that the natural oxide layer on the polished CoCr material (FIG. 3a) is thin and has only a slight enhancement of Cr in it; conventional passivation increases the oxide thickness and Cr/Co ratio in the oxide layer (FIG. 3b), and the "ultra-passivated" (FIG. 3c) has the thickest oxide layer and the highest Cr/Cr ratio in the outer 4 nm of the sample.

Example 2

Clean and polished 25 mm diameter CoCr (F 1537) disks were placed on the center rack (ground potential) of the plasma chamber. The plasma chamber was evacuated to a base pressure of 30 mTorr then backfilled to 300 mTorr with $O_2$ (flow rate=250 sccm). The CoCrMo test disks were treated at an RF power setting of 1000 watts for 1 hour. After allowing the samples in the chamber to cool to room temperature, the chamber was backfilled with dry-$N_2$ and the test disks were removed. The plasma modified CoCrMo disks were then immersed in 6N HCl for 1 hr at room temperature. At this stage the surface chemistry of the modified test disk was evaluated using X-ray Photoelectron Spectroscopy (XPS). More specifically, the XPS analyses were conducted as sputter depth profiles. In the present analysis the sputter removal rate was calculated to be approximately 80 Å/min relative to the $SiO_2$ standard. The resulting depth profile data obtained for the modified test disks is shown in FIG. 4. FIG. 4 contains XPS sputter depth profiles obtained for both the polished and the treated with the inventive process samples. In this example, the inventive process used is $O_2$ plasma treatment at 1000 w, 300 mTorr, 250 smmc for 1 hr+6N HCl for 1 hr treatment. The top plot (FIG. 4a) shows the XPS sputter depth profile representative of a polished CoCr test disk surface. This data shows that the topmost surface of this sample contains approximately equal concentrations of Co (x) and Cr (▲). The data further shows the presence of a very thin (approximately 10 Å) surface oxide layer, which is evident from the rapid decline in the oxygen (■) signal. At a depth of about 20 Å, the A.C. composition measured by XPS reflects the bulk stoichiometry of the alloy. In contrast to the data obtained for the polished sample shown in FIG. 4a, the XPS profile collected for an "ultra-passivated" sample treated with the inventive process (FIG. 4b) indicates that the passivation process used for this sample produced a much thicker oxide layer. In this instance the relative depth of the oxide layer is approximately 5 nm. More importantly, the data further shows that the composition of the surface oxide layer is predominantly Cr-oxide, most likely $Cr_2O_3$. Again, this interpretation is based on the elevated concentrations of Cr (▲) and O (■) within the topmost 4-5 nm coupled with the fact that the cobalt signal (x) was well below 10% (atomic) over this same depth range Example 3

A further proof of the enhanced corrosion resistance of the material after "ultra-passivated" inventive process treatment: FIG. 5a shows the XPS sputter depth profile of a CoCr test disk that was passivated with the inventive process ($O_2$ plasma treatment at 1000 w, 300 mTorr, 250 smmc for 1 hr+6N HCl at room temperature for 1 hr). After above treated sample was put into 6N HCl at 60° C. for 0.5 hr (FIG. 5b) or 6N NaOH for 1 hr (FIG. 5c), the oxide film on the surface has no significant change. Thus, the CoCrMo surface after the inventive treatment can stand corrosive environment.

Example 4

FIG. 6 shows the wear test results from the femur heads treated with the conventional process (30% $HNO_3$ at 60° C. for 0.5 hr) and with the inventive process (30% $HNO_3$ at 60° C. for 0.5 hr+$O_2$ plasma treatment at 1000 w, 300 mTorr, 250 smmc for 1 hr+30% $HNO_3$ at 60° C. for 0.5 hr) respectively. The wear test curves show that the femur head after the inventive treatment reduced 3 folds of wear when compared with the one after the conventional treatment.

Example 5

Table 1 shows the ICP-MS (Inductively Coupled Plasma Mass Spectrometry) data (ICP data) that is obtained from the 20 ml 90% Bovine serum solution which immersed 8 CoCr disks for 7 weeks. The disks are 1 inch in diameter and 0.125 inch in thickness. The solution was placed on a shaker in a 37° C. incubator. The result shows that the disks treated with the inventive passivation reduced the total ion release to 26% of that of the disks treated with conventional passivation.

TABLE 1

Ion Release of the CoCr Disks after Different Passivation in 90% Bovine Serum

| Sample | Co (μg) | Cr (μg) | Cr (μg) | Total Ions (μg) |
|---|---|---|---|---|
| after Conventional Passivation (CP) | 0.116 | 0.014 | 0.018 | 0.148 |
| after Inventive Passivation (IP) | 0.017 | 0.007 | 0.015 | 0.039 |
| IP/CP (%) | 15 | 50 | 83 | 26 |

Example 6

Table 2 shows ICP-MS (Inductively Coupled Plasma Mass Spectrometry) data obtained from immersing the contacting area of a CoCr stem (size 4) and 32 mm head modular system in a 0.9% saline solution which for 16 days. The results show that the implant treated with the inventive passivation reduced the total ion release to 5% of that of the implant treated with the conventional passivation.

TABLE 2 the Comparison of the Ion Release of the CoCr implants Treated with Different Passivation in Saline Solution

| | Released Ions | | | |
|---|---|---|---|---|
| Sample | Cr(ug/ml) | Co(ug/ml) | Mo(ug/ml) | Total ions (um) |
| Conventional Passivation (CP) | 0.010 | 0.200 | ND | 0.210 |
| Inventive Passivation (IP) | 0.004 | 0.008 | ND | 0.012 |
| IP/CP (%) | 40 | 4 | | 6 |

What is claimed:

1. A method for treating a chromium containing component of an orthopedic implant, said method comprising:
    contacting said component with a gas plasma under conditions effective to oxidize at least a portion of the component; and
    contacting said component with an acid to form a treated component;
    wherein the treated component has a surface oxide layer comprising chromium and cobalt oxides where said surface oxide layer is 2.5-8 nm thick and the atomic ratio of Cr/Co ratio >3.

2. The method of claim 1, wherein said component is contacted with said gas plasma before it is contacted with said acid.

3. The method of claim 1, wherein said component is contacted with said acid both before and after said component is contacted with said gas plasma.

4. The method of claim 1, wherein the acid includes nitric acid or hydrochloric acid.

5. The method of claim 4, wherein contacting said component with a acid utilizes an acid concentration of 2-8 M, for 20 min to 2 hr, at a temperature of 0° C.-90° C.

6. The method of claim 5 wherein the time is 30-60 min, temperature is 20° C.-60° C., and the acid concentration is 3-6 M.

7. The method of claim 1, wherein the gas plasma is derived from a gas comprising oxygen.

8. The method of claim 7, wherein the gas comprising oxygen is: $O_2$, $H_2O$ or $H_2O_2$.

9. The method of claim 7, wherein the gas comprising oxygen is $O_2$.

10. The method of claim 1, wherein the component is contacted with the gas plasma for about 5 to about 120 minutes.

11. The method of claim 10, wherein the component is contacted with the gas plasma using a flow rate of 150-350 sccm and a pressure 200 mTorr-400 mTorr.

12. The method of claim 1, wherein the gas plasma is derived from a gas comprising oxidative gases and inert gases.

13. The method of claim 12, wherein the oxidative gases comprise oxygen and inert gases comprise Ar and He.

14. The method of claim 12, wherein the gas plasma comprises at least 3% (v/v) percent oxidative gas.

15. The method of claim 1, wherein said contacting said component with the gas plasma is performed at a power of about 100 to about 1000 watts.

16. The method of claim 15 where the power is 800-1000 watts.

17. The method of claim 1, wherein the component includes a CoCrMo alloy.

18. The method of claim 1, wherein said component has a surface oxide layer up to 20 nm thick.

19. The method of claim 1, wherein said Cr/Co ratio is 3-7.

20. The method of claim 1, wherein said component is a component of a joint replacement prosthesis.

21. The method of claim 1, where said component is a component of a hip or knee replacement prosthesis.

22. The method of claim 1, wherein said surface is at a wear interface.

23. The method of claim 1, wherein the acid is citric acid.

* * * * *